(12) United States Patent
Rocha

(10) Patent No.: US 7,368,132 B2
(45) Date of Patent: May 6, 2008

(54) GLYOXAL/ZINC FIXATIVE

(75) Inventor: Andrew J. Rocha, Long Beach, CA (US)

(73) Assignee: Medical Chemical Corporation, Torrance, CA (US)

( * ) Notice: Subject to any disclaimer, the term of this patent is extended or adjusted under 35 U.S.C. 154(b) by 464 days.

(21) Appl. No.: 10/975,732

(22) Filed: Oct. 27, 2004

(65) Prior Publication Data

US 2006/0088813 A1  Apr. 27, 2006

(51) Int. Cl.
- *A01N 1/02* (2006.01)
- *A01N 35/02* (2006.01)
- *A01N 59/16* (2006.01)
- *G01N 1/30* (2006.01)
- *G01N 33/48* (2006.01)
- *C12N 5/00* (2006.01)
- *C12Q 1/02* (2006.01)

(52) U.S. Cl. ......... 424/641; 424/75; 514/698; 514/705; 514/724; 435/2; 435/40.5; 436/18

(58) Field of Classification Search ......... 514/698; 424/75, 641; 435/2, 40.5
See application file for complete search history.

(56) References Cited

U.S. PATENT DOCUMENTS

| | | | |
|---|---|---|---|
| 4,493,821 A * | 1/1985 | Harrison | 435/40.52 |
| 4,666,699 A | 5/1987 | Slifkin | 435/40.51 |
| 5,290,706 A | 3/1994 | Camiener | 436/174 |
| 5,429,797 A | 7/1995 | Camiener | 422/1 |
| 5,482,676 A | 1/1996 | Camiener | 422/61 |
| 5,504,012 A | 4/1996 | Lipton | 436/176 |
| 5,508,175 A | 4/1996 | Slifkin | 435/40.5 |
| 5,587,157 A * | 12/1996 | Cox et al. | 424/76.5 |
| 5,589,164 A | 12/1996 | Cox et al. | 424/76.5 |
| 5,607,870 A | 3/1997 | Lipton | 436/176 |
| 5,622,696 A | 4/1997 | Camiener | 424/75 |
| 5,736,032 A | 4/1998 | Cox et al. | 424/76.5 |
| 5,874,315 A | 2/1999 | Kraft et al. | 436/176 |
| 5,977,153 A | 11/1999 | Camiener | 514/392 |
| 6,171,259 B1 | 1/2001 | Fisher | 600/549 |
| 6,261,788 B1 | 7/2001 | Cummings et al. | 435/7.22 |
| 6,596,502 B2 | 7/2003 | Lee | 435/7.22 |
| 6,706,290 B1 * | 3/2004 | Kajander et al. | 424/616 |

* cited by examiner

*Primary Examiner*—John Pak
(74) *Attorney, Agent, or Firm*—Cislo & Thomas, LLP

(57) ABSTRACT

This invention provides compositions and methods for fixing a biological sample, particularly fecal samples for diagnosis of parasitic infection. The fixative composition of the present invention comprises glyoxal (pyruvate aldehyde) and zinc sulfate and permits staining of biological samples without use of toxic compounds, such as formaldehyde and mercury-containing compounds. The fixative is compatible with many diagnostic assays, including trichrome stains, hematoxlin, ELISA, fluorescent assays, and lateral flow assays.

18 Claims, No Drawings

GLYOXAL/ZINC FIXATIVE

BACKGROUND OF THE INVENTION

FIELD OF THE INVENTION

The present invention relates to methods and compositions for preserving biological specimens, particularly fecal samples used in diagnosing parasitic infection. A fixative is provided which comprises alcohol, polyvinyl alcohol, zinc sulfate, glyoxal (pyruvate aldehyde), acetate buffer and water. The parasitological fixative does not contain formaldehyde, mercury or other harmful chemicals commonly associated with fixative compositions and permits staining with resolution and contrast comparable to that of mercury-based fixatives.

SUMMARY OF THE INVENTION

Parasitic infections have a long history of causing disease in humans and animals. These include protozoan parasites such as extra-intestinal amoebas, toxoplasmas and trichomonas. In addition, other human parasites include helminths such as roundworm, pinworm, hookworm, shisasomes and tapeworms. Diagnosis of intestinal parasites is generally confirmed by staining and microscopically identifying helminith eggs and larvae or protozoan trophozoites and/or cysts in fecal samples. One problem in diagnosis, however, is the delay between collection and the examination of specimens, which, without a suitable fixative, results in rapid degradation of the specimen. Short of immediate processing, accurate diagnosis thus depends upon obtaining the best fixation of the specimen upon collection. Fixative solutions are therefore routinely used in processing specimens for parasitic diagnosis.

Conventionally, mercury-based fixatives, such as Schaudinn fixative with a mercuric chloride base, have been used as a preservative for staining and subsequent microscopic examination of specimens. While mercury-based fixatives generally provide good definition, they have a number of disadvantages that limit their use. In particular, mercury is toxic and disposal of mercury-containing fixatives is a concern due to the prohibitive cost and the scarcity of disposal companies willing to handle mercury waste. Preservatives comprising formaldehyde or formalin raise similar environmental and health concerns. In addition, formalin and mercury-based preservatives limit the detection techniques that may be used to analyze the preserved specimens. For example, formalin-preserved specimens generally cannot be used with permanent stains and immunoassays utilizing fluorescent labels may become undetectable when formaldehyde is used.

Although non-mercury based fixatives have been developed for use in parasitological diagnosis, the stained specimens exhibit inconsistent and low quality staining, as compared to specimens preserved in mercury-based fixatives. For example, stains that are frequently used in parasitological diagnosis, such as trichrome stain and iron hematoxylin, work well with mercury-based fixatives but do not perform as well with non-mercury based fixatives.

The present invention relates to a mercury-free, formaldehyde-free composition and method for fixing biological specimens, particularly fecal samples, for the detection and identification of parasites, including the detection of helminth larvae, eggs, protozoan trophozoites and cysts, coccidian oocysts and microsporidian spores. The fixative composition does not require albumin to adhere the specimens to microscope slides and yields a staining quality equal to that of mercury polyvinyl alcohol (PVA). The fixative comprises water, acetate buffer, glyoxal (pyruvic aldehyde), zinc sulfate, acetic acid and alcohol, and allows use of a single fixative for all of the diagnostic techniques necessary to identify intestinal parasites. For example, the fixative is compatible with various diagnostic techniques, such as ELISA assays, lateral flow assays, modified Wheatley's Gomorid Trichrome, fluorescent assays, iron hematoxylin stain and concentration procedures.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The fixative compositions and methods of the present invention are useful for preserving biological specimens, particularly samples for diagnosis of parasitic infections, including fecal samples. The fixative composition preferably comprises: (1) from about 0.00 milliliter ("ml") to about 300 ml per liter of reagent alcohol, more preferably from about 50.0 ml to about 250 ml, and most preferably about 225 ml per liter ("1") of reagent alcohol; (2) preferably from about 10 grams ("g") per liter to about 100 grams per liter, more preferably from about 25 g/l to about 75 g/l and most preferably about 40 grams per liter, of polyvinyl alcohol (e.g. Elvanol® 51-05 available from Dupont®); (3) between about 10 grams per liter to about 150 grams per liter, more preferably between about 50 g/l and about 100 g/l, and most preferably about 75 grams per liter of zinc sulfate; (4) from about 1.0 grams per liter to about 50 grams per liter, more preferably between about 5.0 g/l and about 25 g/l, and more preferably about 12 grams per liter of glyoxal (pyruvate aldehyde); (5) from about 0.01 M/l to about 1.0 M/l buffer, more preferably between about 0.05 M/l to about 0.5 M/l buffer, and most preferably about 0.1 M/liter buffer; and (6) water (QSAD).

The buffer used with the fixative of the instant invention is preferably an acetate buffer, although other buffers may be suitable, particularly buffers having a pKa of about 6. Sodium acetate, if used in the buffer, is preferably anhydrous. By way of example only, a suitable buffer may comprise about 2.43 grams per liter of sodium acetate and about 4.23 grams per liter of acetic acid. The fixative composition of the present invention is preferably is at a pH of from about 3.0 to about 6.0, is more preferably at a pH of about 3.5 to about 5.0 and is most preferably at a pH of about 4.3.

The zinc sulfate, as used in the fixative composition of the present invention, is preferably a heptahydrate, A suitable reagent alcohol may comprise ethyl alcohol, methyl alcohol and/or isopropyl alcohol, or other low molecular weight alcohols. By way of example only, a suitable reagent alcohol solution may comprise: (1) from about 0% to about 100% of ethyl alcohol, more preferably from about 50% to about 95% ethyl alcohol, and most preferably about 90% ethyl alcohol;

(2) from about 0% to about 100% of methyl alcohol, more preferably from about 1% to about 20% methyl alcohol, and more preferably comprises about 5% methyl alcohol; and (3) from about 0% to about 100% of isopropyl alcohol, more preferably from about 1% to about 20% isopropyl alcohol, and most preferably comprises about 5% isopropyl alcohol.

A preferred method of making the fixative composition comprises a first step of adding the buffer salts and zinc sulfate in sufficient water to dissolve the buffer salts and zinc sulfate and form a zinc sulfate solution. Next, polyvinyl alcohol is dissolved in water to form a polyvinyl alcohol solution, which is then heated to between about 60° C. and about 100° C., and more preferably to about 90° C., preferably with constant stirring. The temperature of the polyvinyl alcohol solution is maintained above about 90° C. for between about fifteen minutes and about sixty minutes, and more preferably for about thirty minutes. The polyvinyl alcohol solution is then preferably transferred to a mixing tank with stirring. The polyvinyl alcohol solution and zinc sulfate solution are then mixed and the reagent alcohol added. Next, water is added QSA and the resulting fixative composition is preferably filtered.

To use the fixative composition, a fecal specimen, or other biological specimen, is collected and placed in an effective amount of fixative. A preferred ratio of fixative composition to sample is preferably from about one part fixative composition to about one part sample, is more preferably two parts fixative composition to one part sample, and is most preferably from about three parts of fixative composition to about one part of sample, although other ratios may be suitable. For example, a preferred ratio of fixative composition to sample may be about 1.0 ml fixative/gram sample, more preferably may be about 2.0 ml fixative/gram of sample and most preferably may be about 3.0 ml fixative composition/gram of sample. The sample may be left in the fixative composition for hours, days or may be preserved for months as needed, depending upon the need for evaluation or storage.

Biological samples processed according to the method of the present invention are compatible with various diagnostic techniques, including trichrome staining, modified trichrome staining, modified acid fast staining, hematoxylin staining, ELISA, lateral flow assays, fluorescent stains and immunoassays. Once the specimen has been fixed with the fixative of the present invention, the specimen may be processed for evaluation.

For example, biological specimens, particularly fecal specimens, may be processed and evaluated using a procedure incorporating Mayer's Hematoxylin. In one example using Mayer's Hematoxylin, an aliquot of a specimen mixture comprising the specimen and fixative composition is placed into a suitable container (such as, for example, a centrifuge tube or a round bottom tube). The volume of the aliquot is preferably between about 1.0 ml to about 2.0 ml, although other size aliquots may be processed. Next, from about 5.0 ml to about 20.0 ml, and more preferably about 7 ml to about 10 ml, of normal saline (sodium chloride) is added to the container holding the specimen mixture. The specimen mixture is then mixed well by, for example, capping and shaking the container.

Next, the specimen mixture is preferably centrifuged at from about 200×g to about 800×g, and is more preferably centrifuged at about 500×g, for about two minutes to about twenty minutes, and more preferably for about ten minutes. After centrifuging, the resulting liquid supernatant is discarded. In the preferred embodiment, there will be approximately 0.5 ml to about 0.75 ml of specimen, or fecal sediment, at the bottom of the container or tube, although lesser or greater yields may result depending on various factors, such as the aliquot volume. The specimen or fecal sediment is then preferably mixed, for example with an applicator stick, and is preferably smeared onto at least one microscope slide and preferably air dried for further processing. The resulting smears are preferably relatively thin to permit suitable drying and examination.

The slides comprising the smears may then be placed into a Mayer's Hematoxylin solution. For optimal staining, the slides may be put through two changes of Mayer's Hematoxylin, for approximately twenty minutes to about ten minutes and more preferably for about fifteen minutes each change, although other times may be suitable depending upon the Hematoxylin solution used. The slides are then preferably placed into a water substitute (e.g. Scott's Tap Water Substitute™ from BBC Biochemical) for about thirty seconds to about two minutes, and more preferably for about one minute.

Next, the slides are preferably run through a series of alcohols into a Xylene substitute, or similar, and air-dried. By way of example, the slides may be run through two changes of 70% alcohol for between about one minute to about five minutes, and more preferably for about two minutes each change; two changes of 100% alcohol for between about one minute to about five minutes, and more preferably for about two minutes each change; and in two changes of Xylene for between about one minute to about five minutes, and more preferably for about two minutes each change.

If more than a few slides, or staining dishes with racks of slides are used, the times in alcohol and Xylene are preferably increased. For example, if a staining dish and slide racks are used, the slide rack is preferably brought through two changes of 70% alcohol for between about two minutes to about ten minutes, and more preferably for about three minutes each change; two changes of 100% alcohol for about two minutes to about ten minutes, and more preferably about three minutes each change; and through two changes of Xylene for between about five minutes to about ten minutes for each change. The slides are then preferably air-dried.

Once dried, the slides may be prepared for viewing under a microscope, such as for example, a microscope with an oil immersion lens. Where an oil immersion lens is used, a suitable amount of immersion oil, such as about one drop, may be placed onto the dried smear for about five minutes before viewing. A coverslip may then be placed on top of the smear, and another drop of immersion oil placed on top of the coverslip for viewing with the immersion oil lens.

Specimens, including fecal specimens, fixed using the fixative of the present invention may also be evaluated for parasitic diagnosis using Wheatley's Modified Gomorid Trichrome stain. In one example of this procedure, a specimen to be evaluated is placed in a container with the fixative. Prior to staining, between about 8 to about 10 drops of a surfactant may be added to the container. If a surfactant is added, the contents are preferably vortexed for about thirty seconds or shaken vigorously. The specimen may then be placed in a vial that is attached to a concentration device.

Once concentrated, the specimen is preferably centrifuged for about ten minutes at approximately 500×g and decanted. The specimen sediment is spread onto a microscope slide and allowed to dry completely (preferably for approximately thirty minutes on a heat block or overnight at room temperature). Once dried, the prepared slide may be immersed in a suitable trichrome stain, such as Wheatley's Modified Gomorid Trichrome stain, for between about 8 minutes to about 10 minutes. After staining, the slide is preferably dipped in acid alcohol solution and removed immediately. The slide is then preferably placed in two changes of 100% alcohol for about two minutes to about five minutes and run through two changes of Xylene, or a Xylene substitute (e.g. Hemo-DE® available from Scientific Safety Solvents). Any remaining sediment may be used to perform further analysis. For example, saline and about 3-5 milliliters of ethyl acetate, or other ether substitute, may be added to a sample of the remaining sediment. The sample is then centrifuged for about ten minutes at 500×g and decanted. The sediment sample may then be used to prepare wet mounts and slides for direct fluorescent antibody evaluation (or "DFA") procedures.

The fixative of the present invention saves space and time in that it can be stored and used directly from a single vial and because it permits assays to be run with one fixative solution rather than different or multiple solutions. For example, specimens prepared with the fixative of the instant invention can be analyzed using various diagnostic techniques, such as ELISA assays, lateral flow assays, modified Wheatley's Gomorid Trichrome, fluorescent assays, iron hematoxylin stain and concentration procedures. Also, using the fixative of the instant invention, it is not necessary to apply albumin to the slides to keep the specimen from washing off of the slide.

The fixative of the present invention does not require formaldehyde or other toxic compounds, such as mercury or mercury salts. While the present invention has been described with regards to particular embodiments, it is recognized that additional variations of the present invention may be devised without departing from the inventive concept.

What is claimed is:

1. A mercury-free, formaldehyde-free fixative composition for preserving a biological specimen, comprising:
   a. low molecular weight alcohol, which is present in the composition in an amount that is greater than 0 to about 300 milliliters per liter;
   b. from about 10 grams per liter to about 100 grams per liter of polyvinyl alcohol;
   c. from about 10 grams per liter to about 150 grams per liter of zinc sulfate;
   d. from about 1 gram per liter to about 50 grams per liter of glyoxal;
   e. from about 0.01 M per liter to about 1.0 M per liter of buffer; and
   f. water.

2. The fixative composition of claim 1, comprising:
   a. from about 50 milliters per liter to about 300 milliliters per liter of low molecular weight alcohol;
   b. from about 10 grams per liter to about 100 grams per liter of polyvinyl alcohol;
   c. from about 10 grams per liter to about 150 grams per liter of zinc sulfate;
   d. from about 1 gram per liter to about 50 grams per liter of glyoxal;
   e. from about 0.01 M per liter to about 1.0 M per liter of buffer; and
   f. water.

3. The fixative composition of claim 2, comprising:
   a. between about 50 milliliters and about 250 milliliters of low molecular weight alcohol;
   b. between about 25 grams per liter and about 75 grams per liter of polyvinyl alcohol;
   c. from about 50 grams per liter to about 100 grams per liter of zinc sulfate;
   d. from about 5 grams per liter to about 25 grams per liter of glyoxal;
   e. from about 0.05 M per liter to about 0.5 M per liter of buffer; and
   f. water.

4. The fixative composition of claim 3, comprising about 225 milliliters per liter of low molecular weight alcohol.

5. The fixative composition of claim 3, comprising about 40 grams per liter of polyvinyl alcohol.

6. The fixative composition of claim 3, comprising about 75 grams per liter of zinc sulfate.

7. The fixative composition of claim 3, comprising about 12 grams per liter of glyoxal.

8. The fixative composition of claim 3, comprising about 0.1 M per liter of buffer.

9. The fixative composition of claim 1, wherein the buffer has a pKa of about 6.

10. The fixative composition of claim 1, wherein the buffer is an acetate buffer.

11. The fixative composition of claim 1, wherein the pH is from about 3.0 to about 6.0.

12. The fixative composition of claim 11, wherein the pH is between about 3.5 and about 5.0.

13. The fixative composition of claim 12 wherein the pH is about 4.3.

14. A formaldehyde-free, mercury-free fixative composition for preserving biological specimens, comprising:
   a. from about 200 milliliters per liter to about 250 milliliters per liter of low molecular weight alcohol;
   b. from about 25 grams per liter to about 75 grams per liter of polyvinyl alcohol;
   c. from about 50 grams per liter to about 100 grams per liter of zinc sulfate;
   d. from about 5 grams per liter to about 25 grams per liter of glyoxal;
   e. from about 0.05 M per liter to about 0.5 M per liter of buffer; and
   f. water, wherein the pH of the fixative composition is from about 3.5 to about 5.0

15. The fixative composition of claim 14, wherein the pH is about 4.3.

16. A formaldehyde-free, mercury-free fixative composition for preserving biological specimens, comprising:
   a. about 225 milliliters per liter of low molecular weight alcohol;
   b. about 40 grams per liter of polyvinyl alcohol;
   c. about 75 grams per liter of zinc sulfate;
   d. about 12 grams per liter of glyoxal;
   e. about 0.10 M per liter of buffer; and
   f. water.

17. The fixative of claim 16, wherein the pH is from about 3.5 to about 5.0.

18. The fixative of claim 17, wherein the pH is about 4.3.

* * * * *